(12) United States Patent
Rosenblatt (10) Patent No.: US 7,931,612 B2
(45) Date of Patent: Apr. 26, 2011

(54) BYPASS VALVE

(75) Inventor: Peter L. Rosenblatt, Newton, MA (US)

(73) Assignee: Rosenblatt Associates, LLC, West Newton, MA (US)

( * ) Notice: Subject to any disclaimer, the term of this patent is extended or adjusted under 35 U.S.C. 154(b) by 655 days.

(21) Appl. No.: 11/994,027

(22) PCT Filed: Jun. 27, 2006

(86) PCT No.: PCT/US2006/024864
§ 371 (c)(1),
(2), (4) Date: Dec. 27, 2007

(87) PCT Pub. No.: WO2007/002613
PCT Pub. Date: Jan. 4, 2007

(65) Prior Publication Data
US 2010/0217232 A1    Aug. 26, 2010

Related U.S. Application Data

(60) Provisional application No. 60/694,401, filed on Jun. 27, 2005.

(51) Int. Cl.
*A61M 1/00* (2006.01)
*A61M 5/14* (2006.01)

(52) U.S. Cl. .................................. 604/34; 604/250

(58) Field of Classification Search ............... 604/6.1, 604/9, 32, 33, 34, 99.02, 99.03, 99.04, 167.03–167.05, 604/236, 232, 247, 248, 249, 288.03, 323, 604/335
See application file for complete search history.

(56) References Cited

U.S. PATENT DOCUMENTS
4,248,223 A   2/1981   Turner et al.
5,910,135 A   6/1999   Hadzic et al.

OTHER PUBLICATIONS

International Search Report for PCT/2006/024864.
Written Opinion for PCT/2006/024864.

*Primary Examiner* — Manuel A. Mendez
(74) *Attorney, Agent, or Firm* — Scott E. Kamhols; Foley Hoag LLP (57) ABSTRACT

An intravenous fluid administration apparatus may include a proximal conduit having a spiked first end for attaching to a reservoir of fluid and a second end, a distal conduit, an intermediate conduit network providing fluid communication from the proximal conduit's second end to the distal conduit and including first and second constituent conduits that provide parallel paths from the proximal conduit to the distal conduit, a flow regulator so engaged with the first constituent conduit as to enable control of fluid flow therethrough, and a pressure-responsive valve so interposed in the second constituent conduit as to permit flow from the proximal conduit to the distal conduit through the second constituent conduit when a fluid pressure difference across the valve exceeds a threshold and to prevent such flow when the difference does not exceed the threshold.

20 Claims, 10 Drawing Sheets

BYPASS VALVE

CROSS-REFERENCE TO RELATED APPLICATION

This application is the National Stage of International Application Ser. No. PCT/US2006/024864, filed Jun. 27, 2006, which claims the benefit of U.S. Provisional Application Ser. No. 60/694,401, filed Jun. 27, 2005, the entire contents of which are hereby incorporated herein by this reference.

BACKGROUND

Intravenous fluids are administered in almost all situations where invasive procedures are performed, where patients require repeated doses of injectable medications, where fluids or blood products are administered, and where a variety of tests are performed, as well as elsewhere. In order to regulate the volume of intravenous fluids that flow into a patient over a given period of time, thumb-wheel compression regulators are universally used. These thumb-wheel regulators (TWR) are manufactured in all intravenous fluid system tubing sold in the United States. Though the TWR is effective in controlling the rate of fluid infusion, it also acts as a restrictor when fluids need to be given rapidly. Though the TWR may be dialed "open" during this period, it may be cumbersome, especially when only an acute "bolus" of fluid is required, e.g., fluid used to flush an emergency drug into the patient.

Standard intravenous lines typically include: a) a proximal "spike and drip chamber" which is used to puncture a latex (or latex like) diaphragm on an intravenous fluid bag or bottle, or on a medication bottle, b) a length of PVC tubing, c) a TWR which is used to regulated the flow of fluid from the raised bag or bottle, and d) a distal connector which may be attached to a compatible intravenous catheter, or other components.

These systems allow the administration of fluids and drugs at a relative rate. The rate of fluid flow will depend on a) the height of the intravenous bag or bottle above the patient (e.g., gravity dependent), b) the set point of the TWR, c) the internal diameter of the intravenous catheter and d) resistance at the catheter-patient interface. Maximal flow will occur with the intravenous bag or bottle raised as high as the tubing and extension tubing will allow, a completely disengaged TWR, a large diameter intravenous catheter and a zero resistance catheter-patient interface.

Because of the limit of the length of tubing, the availability of large veins to accept large diameter catheters and non-zero resistance at the catheter-patient interface as flow through these systems may be slow. When flow is too rapid, the TWR is used to apply a restriction to flow.

When a drug must be delivered to the patient via the intravenous system, it is typically injected into an intravenous port or at the three-way stop cock. Once within the intravenous line, the rate of fluid flow of fluids from the intravenous bag or bottle will determine how rapidly the medication reaches the patient. This rate may not be rapid enough for the clinical situation. If the TWR is restricting flow, the caregiver may disengage the TWR, and then reengage it after he or she believes enough fluid flow has carried the medication into the patient. Often, and especially if flow in the system remains restricted after the disengagement of the TWR, a syringe is used at the injection port or three-way stop cock, to withdraw fluid (with negative pressure applied to the syringe) from the intravenous bag or bottle, which is then injected into the patient in order the "bolus" the medication to the patient (this is virtually impossible if the TWR is partially or fully engaged). Another way that flow may be increased is by squeezing the intravenous bag, creating a positive pressure force. If the TWR is not reengaged, the patient will continue to receive increased fluids, which, in some circumstances, may be detrimental.

In the neonate and infant population fluids are carefully regulated. Failure to reengage a TWR after a drug delivery can be devastating. Additionally, in this patient population, small boluses of fluid (e.g., 5 to 10 cc) may be used therapeutically (e.g., for hypotension). This requires constant disengage-reengagement of the TWR. Again, an error here may be devastating.

SUMMARY

The present disclosure describes a system for bypassing the TWR to allow rapid fluid (liquid) bolus injection. The system may allow an operator to withdraw (from an intravenous fluid bag) and inject a small amount of fluid through the intravenous line, without adjusting the TWR, to aid in medication delivery, improve patient care and save the caregivers time and energy.

DETAILED DESCRIPTION

The present disclosure provides a system for acutely bypassing the flow restriction of the universally used thumb-wheel regulator (TWR) on intravenous fluid administration lines. This bypass may be required when an emergency medication is administered to the patient via an established intravenous infusion line, as well as when non-emergency medications are given, or in other circumstances in which the administration of a bolus is desired.

The Intravenous Fluid Bypass Valve (IVFBV) is an integral TWR-valved conduit. The IVFBV may function as a TWR in its neutral state. When a significant negative pressure is applied distal to the IVFBV (e.g., by a syringe attached to the intravenous port or three-way stopcock), the conduit valve opens and allows free flow of fluid past the TWR portion. When negative pressure ceases, the valve closes and the TWR once again functions to restrict flow. When positive pressure is applied to the valve (e.g., by the squeezing of the intravenous bag) the valve opens, allowing increased flow. The valve closes when positive pressure is released. Flow may then resume at the rate set by the TWR without having to re-set the TWR.

In one exemplary embodiment, a bypass valve may include: a) a Y-split in the intravenous tubing, b) an opaque or clear housing split by a septum into two longitudinal chambers, c) a TWR wheel on the lateral surface of one chamber, which progressively restricts flow in the intravenous tubing as its position is changed, d) a one-way, pressure operated valve in the second chamber (detailed below), and e) Y-rejoining of the intravenous tubing as it leaves the chamber.

The one-way valve may be selected, constructed, and/or arranged so that it will not open below a threshold pressure difference across the valve. The threshold pressure difference may be so selected as to exceed the normal pressure difference across the valve created by the fluid in the tubing and bag above the valve. In this way, the pressure of ordinary flow will not be sufficient to open the valve; instead, additional pressure must be applied to open the valve. The additional pressure may be supplied, for example, by squeezing the IV bag proximal to the valve or by suctioning using a syringe distal to the valve.

The one-way, pressure operated valve may reside completely within a length of intravenous like PVC tubing, within the second chamber of the housing. This tubing is of larger diameter than the remaining tubing of the intravenous system to allow for flow restriction caused by the valve mechanism. The proximal and distal ends of the valve are demarcated by annular rings of PVC (molded as part of the valve tubing). The centers of these annular rings are the lumens of fluid flow into and out of the valve. A ball bearing made of stainless steel, plastic, or other material sits beneath the proximal (intravenous bag/bottle side) ring, obstructing the lumen in the neutral state. Beneath the ball bearing is a spring, holding the ball bearing into the lumen of the proximal annular ring. The distal end of the spring is held in place on the distal annular ring.

Regardless of the position of the TWR, as negative pressure is applied to the distal system (via a syringe at the distal injection port or stopcock), or as positive pressure is applied to the proximal system (via pressure on the intravenous bag), the valve opens and flow is momentarily increased. Once negative or positive pressure is relieved, the valve closes, and the system is once again regulated by the position of the TWR. The rate of fluid flow is immediately returned to the rate which had been set by the TWR previously.

The IVFBV may be an integral part of an intravenous administration system, acting as the TWR for the system. The IVFBV may also be used as an "add-on" device between the intravenous administration system and the patient (then used as an add-on the TWR of the intravenous administration system would be disengaged at all times.

Additional components which may be added include a) a one way flow valve, b) an injection port for medication administration, c) a stop-cock, such as a three-way stop-cock, or d) extension tubing.

The tubing distal to the IVFBV may include a sideport for receiving a needle or needleless syringe for addition of fluid to the intravenous line.

In some embodiments, the bypass valve need not be enclosed by a housing.

In some embodiments, a bypass valve may include a one-way pressure-operated valve as described connected to proximal and distal lengths of tubing. The proximal tubing may connect to one branch of a proximal Y-split, with the stem of the proximal Y-split having a spike for introducing into a fluid bag. The other branch of the proximal Y-split may be configured to receive the tubing of a generic intravenous set that would normally be attached directly to the fluid bag. The distal tubing may incorporate or connect to a distal connector, such as a Y-split, a stopcock, or other connector, that engages a downstream device, such as a catheter, injection port, etc. The connector may be, for example, a luer lock or a needle, among other things. The distal connector may also receive the tubing of a generic intravenous set that would normally be attached to the downstream device. This arrangement may be well-suited for "retrofitting" existing generic intravenous sets with a bypass valve.

An alternative configuration of the IVFBV employs a plunger-shaped valve stop. The annular PVC rings and spring are similar to that described above. The plunger handle faces downwards within the spring. The plunger head sits on top of the spring and, in the neutral position, seals against the underside of the proximal annulus. Other valves may be used in place of the ball- and plunger-valves described, such as disc valves, check valves, and flapper valves, among others.

In some embodiments, the IVFBV may include a clip mechanism that pinches and distorts the proximal PVC annular ring from a circular to an oval opening. This clip would allow for the conduit chamber to fill with fluid when the IV fluid bag is spiked, in order to rid the entire system of air before connecting the system to the patient. The IVFBV may also include an air vent to facilitate purging the line of air when it is hooked to an IV bag. The vent may be a one-way valve that permits air to leave the system but not to enter it. The IVFBV may also include a bulb pump to facilitate drawing up and administering a bolus.

Other examples of one-way valves include a duck valve and a one-way flap valve.

Figure 1:
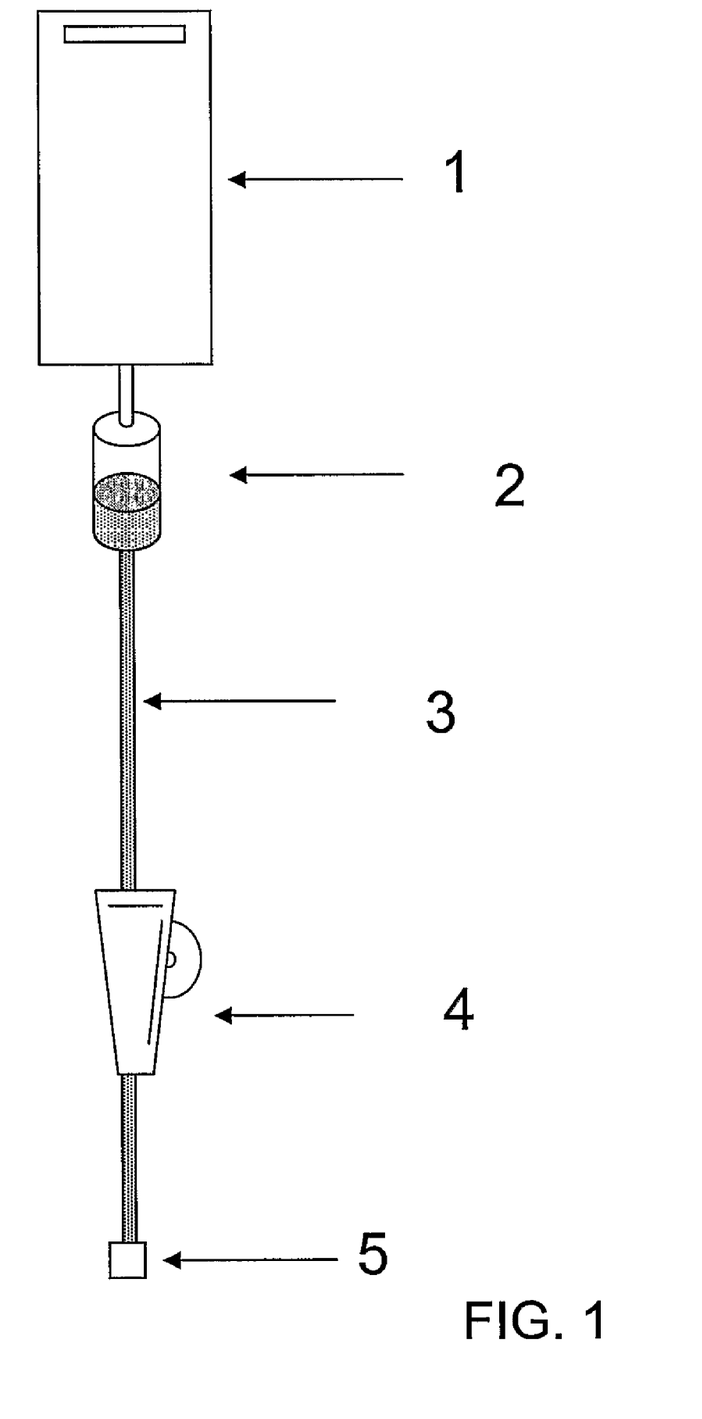
FIG. 1 depicts a generic intravenous administration set.

FIG. 1 shows a standard intravenous administration system. Universally, these include a fluid bag 1 spike and drip chamber 2, intravenous tubing 3, TWR 4, and an adaptor 5 for a compatible intravenous catheter.

Figure 2:
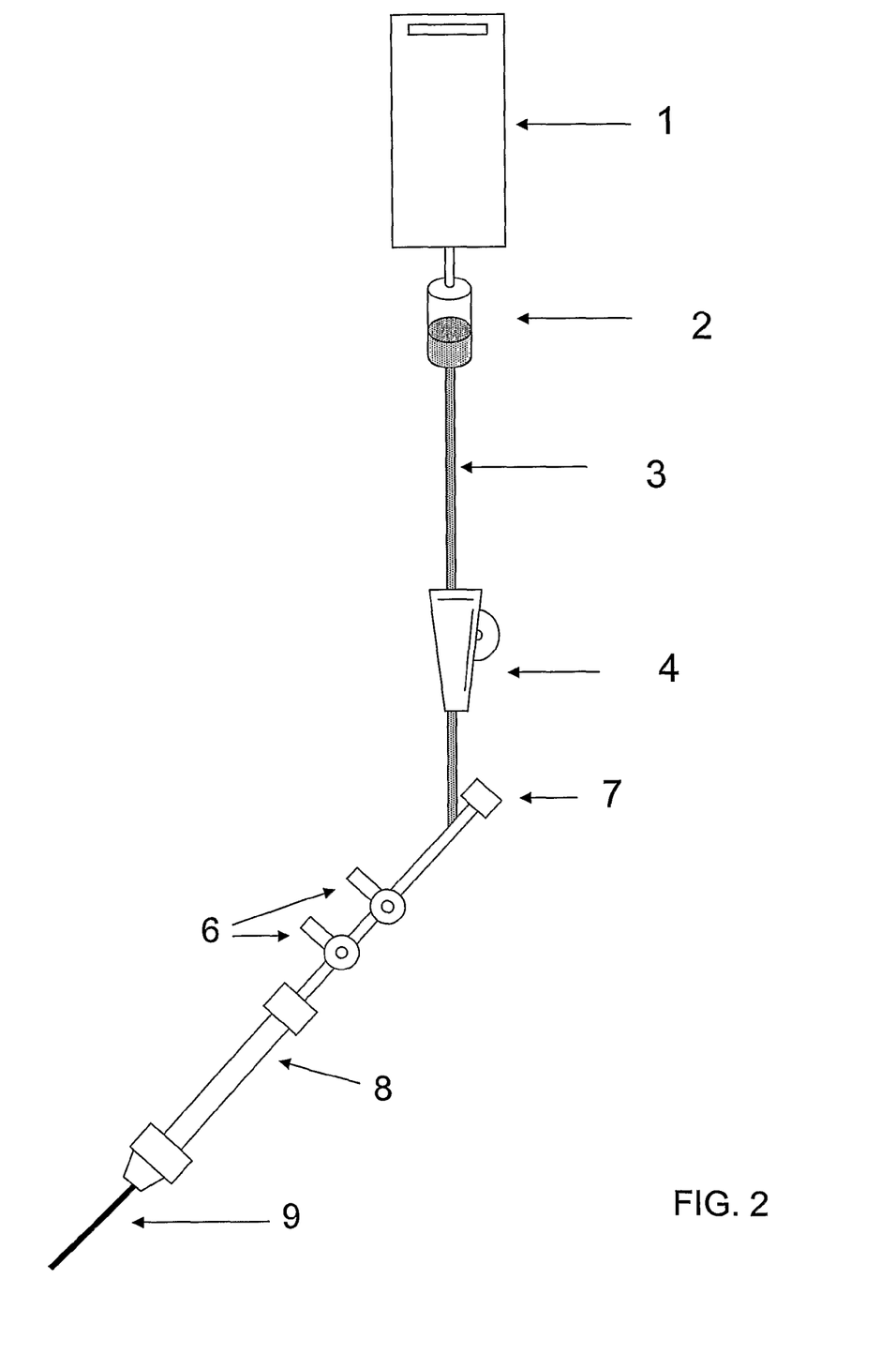
FIG. 2 depicts a generic intravenous administration set with add on components.

FIG. 2 shows the additional components that are commonly added to the standard intravenous administration set, including a three-way stopcock 6, injection port 7, extension tubing 8, and intravenous catheter 9.

Figure 3:
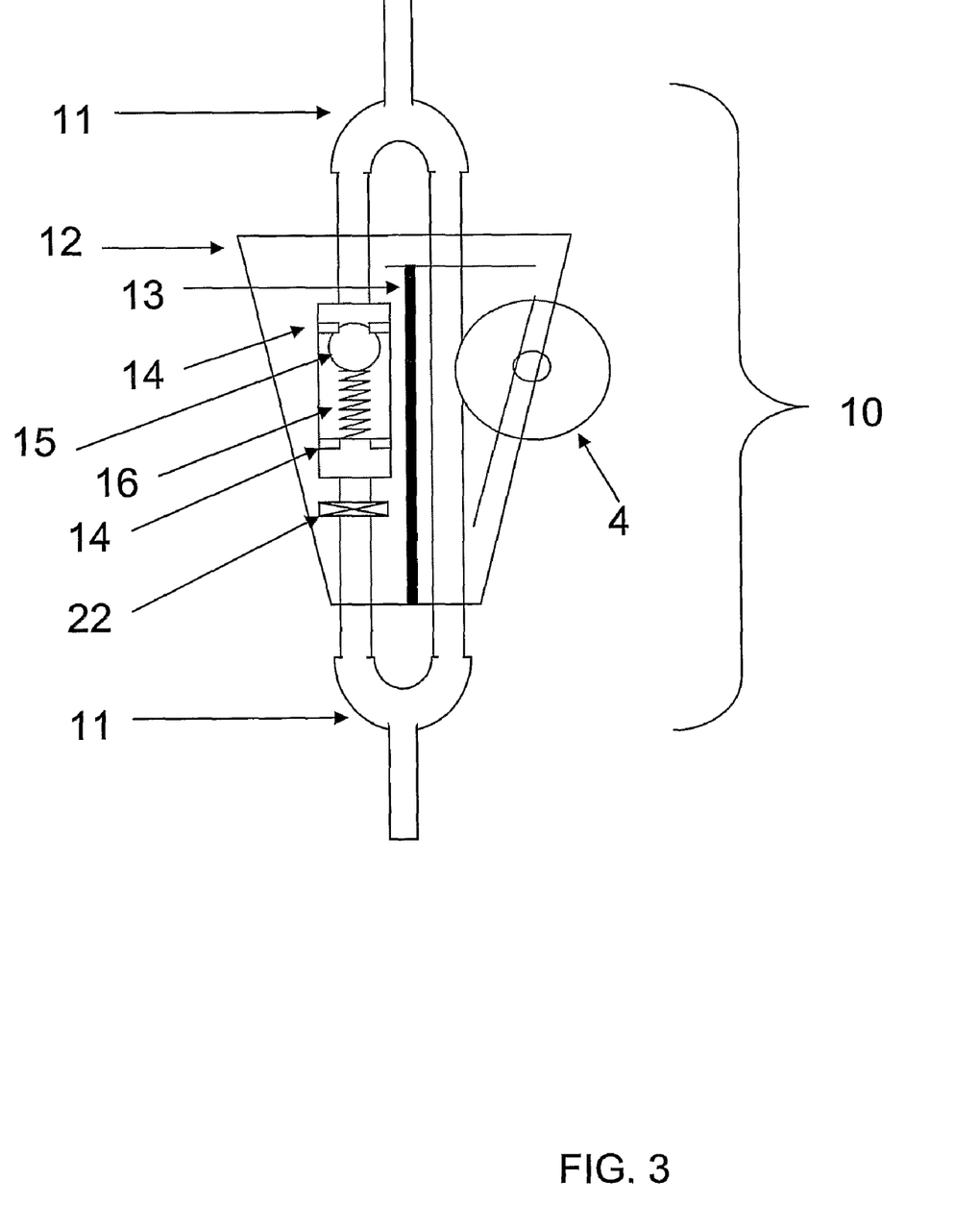
FIG. 3 depicts an exemplary embodiment of a bypass valve having a ball bearing and spring mechanism.

FIG. 3 shows the IVFBV with the Y-split in the IV tubing 11, the housing 12, including a septum 13 within the housing, the conduit bypass valve 10, which includes the two PVC rings 14, a ball bearing 15, and spring 16. The TWR 4 adjusts the flow of fluid in a parallel tubing. An air vent 22 provides a route for air to leave the system as the tubing fills with fluid.

Figure 4:
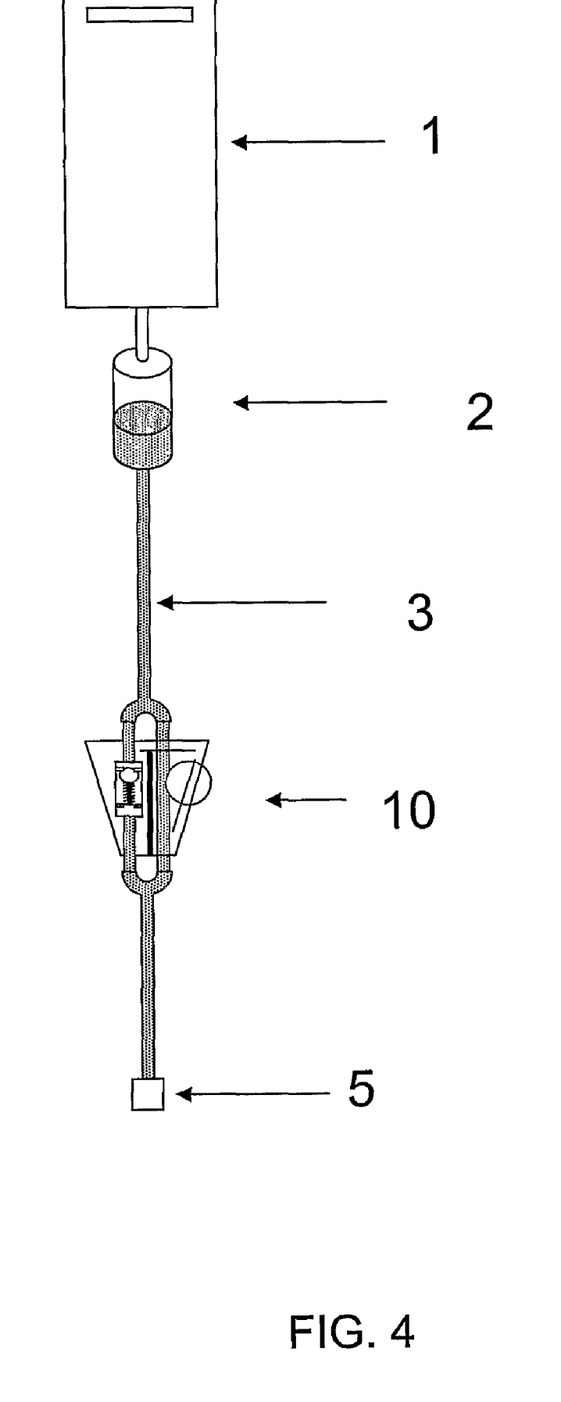
FIG. 4 depicts an intravenous administration set that includes a bypass valve.

FIG. 4 depicts an intravenous administration set that includes a bypass valve 10.

Figure 5:
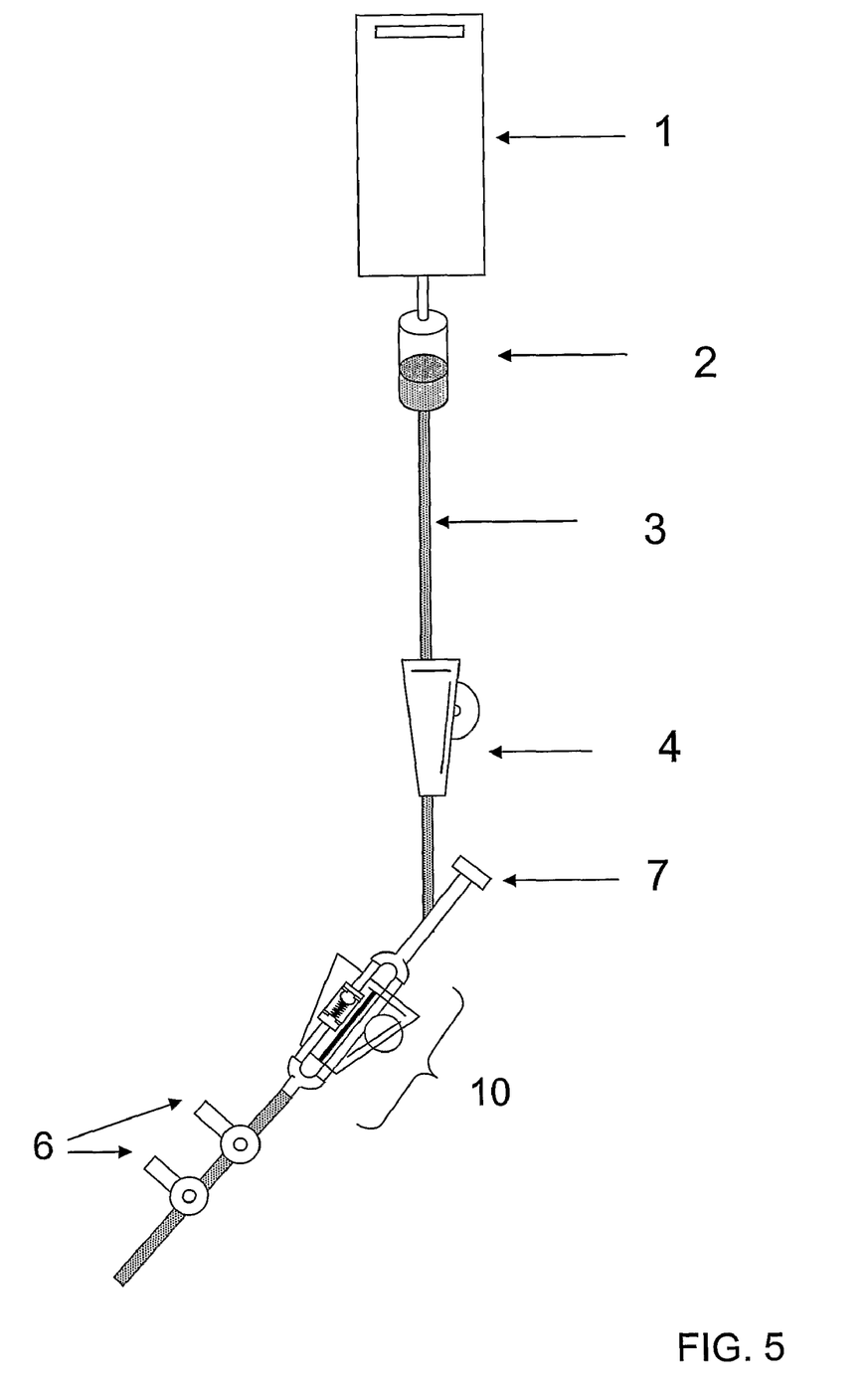
FIG. 5 depicts an exemplary embodiment of a bypass valve as an add on component to a generic intravenous administration set.

FIG. 5 shows the IVFBV as it might be used as an add-on component to a standard intravenous administration set.

Figure 6:
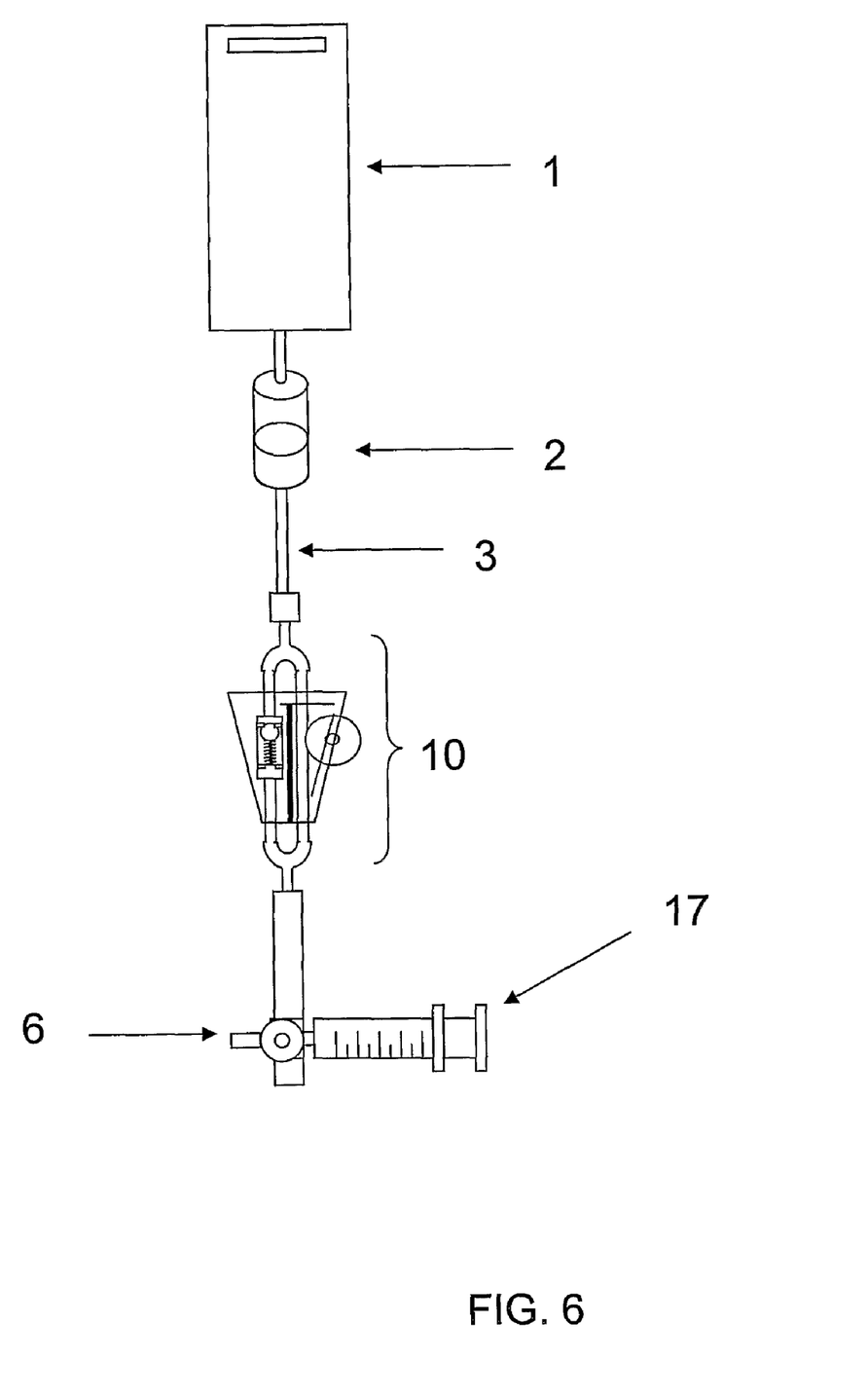
FIG. 6 depicts an exemplary embodiment of a bypass valve as an integral part of an intravenous administration set.

FIG. 6 shows the IVFBV manufactured as an integral part of an intravenous administration set, with a syringe 17 attached to the stopcock 6.

Figure 7:
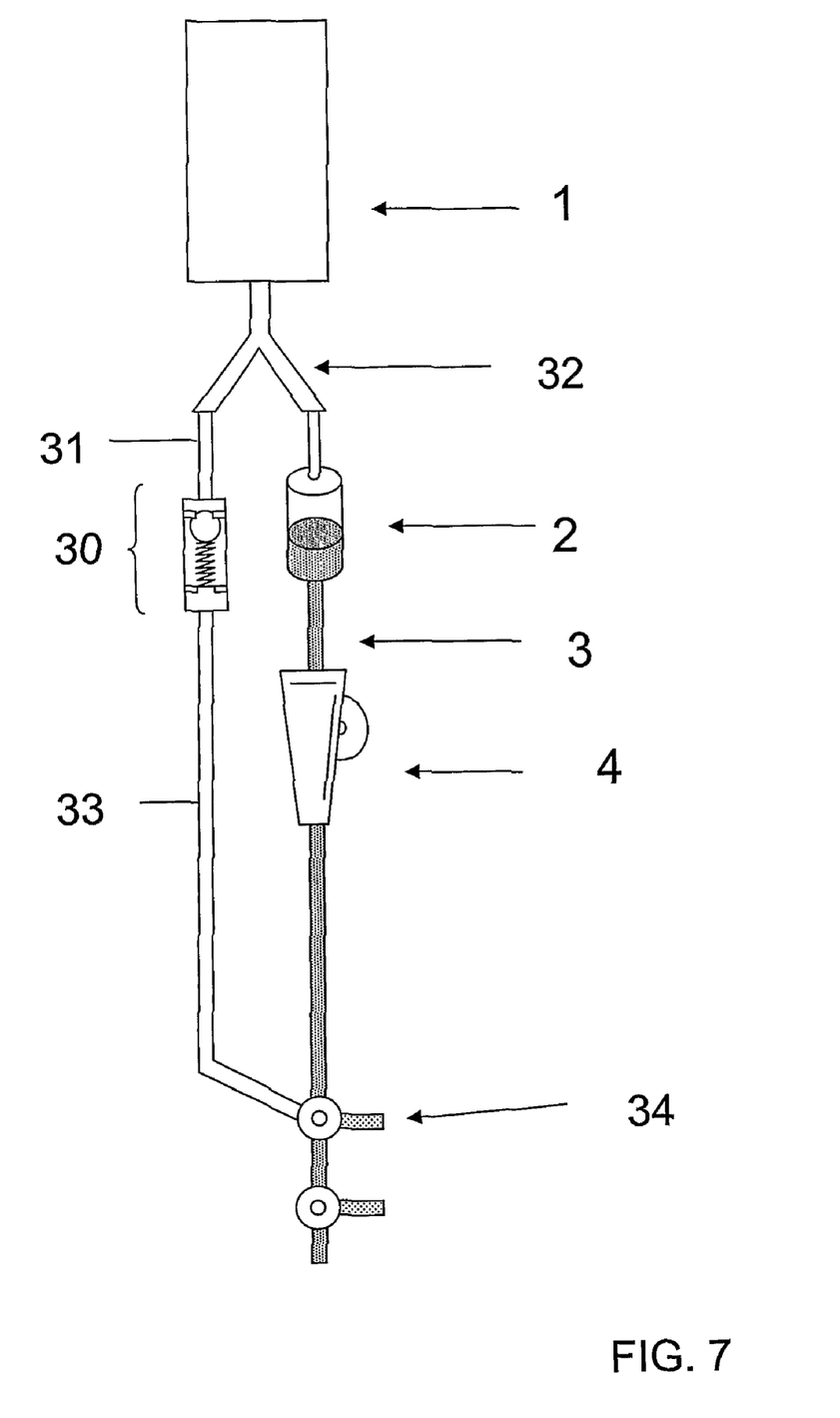
FIG. 7 depicts an exemplary embodiment of a one-way pressure-operated valve separate from a thumb-wheel regulator.

FIG. 7 depicts a bypass valve in which the one-way pressure-operated valve 30 is separate from the TWR 4. The pressure-operated valve is attached to proximal tubing 31 which is connected to one branch of proximal Y-split 32. The stem of the proximal Y-split is inserted in an IV fluid bag. The pressure-operated value is also attached to distal tubing 33 which is connected to distal connector 34 (shown as a stopcock). A traditional IV set extends from the other branch of the proximal Y-split to the distal connector.

Figure 8:
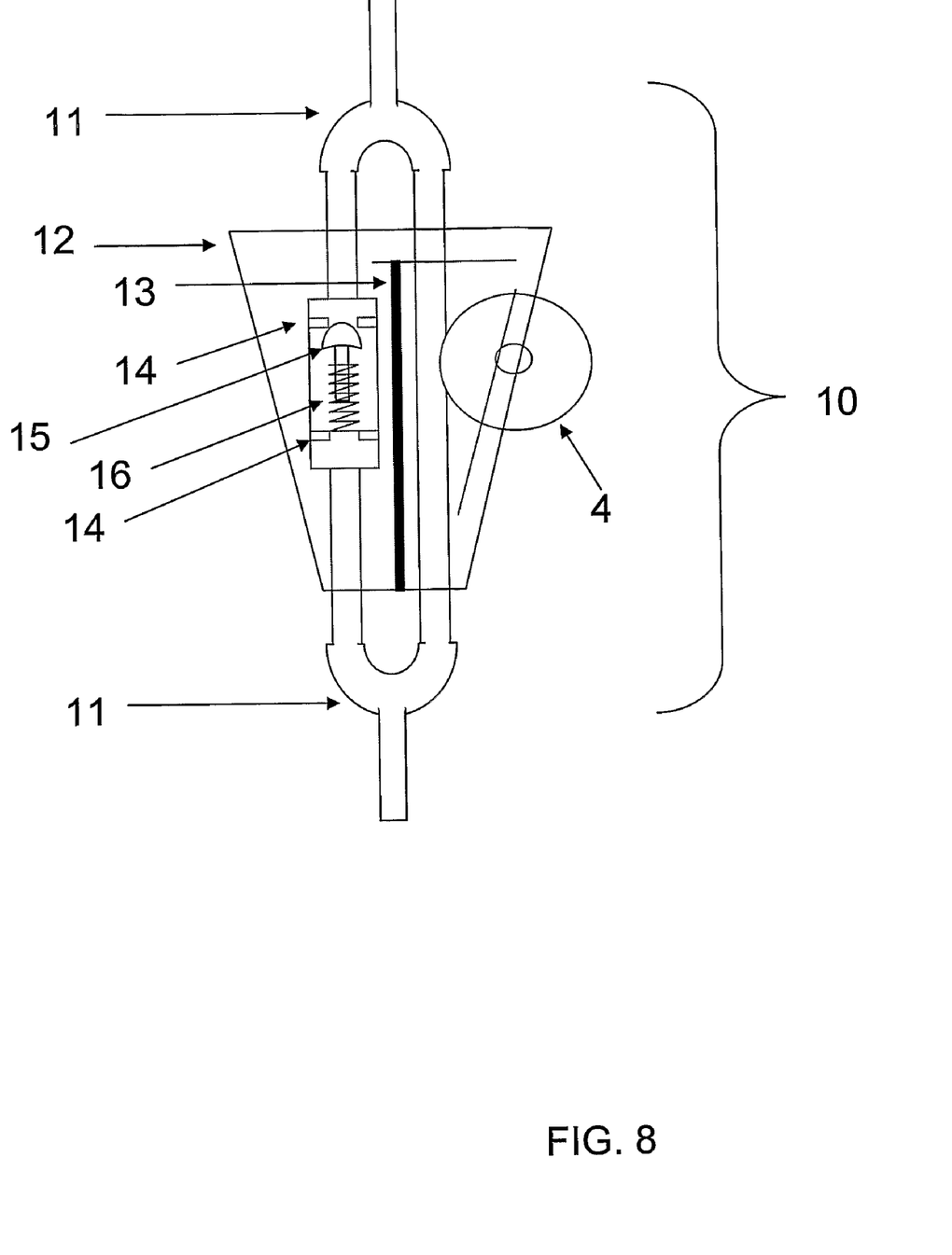
FIG. 8 depicts an alternative exemplary embodiment of a bypass valve with a plunger and spring mechanism.

FIG. 8 demonstrates an alternative embodiment with annular PVC rings and the spring in a position similar to that described above. The plunger handle 18 faces downwards within the spring. The plunger head 19 sits on top of the spring and, in the neutral position, seals against the underside of the proximal annulus.

Figure 9:
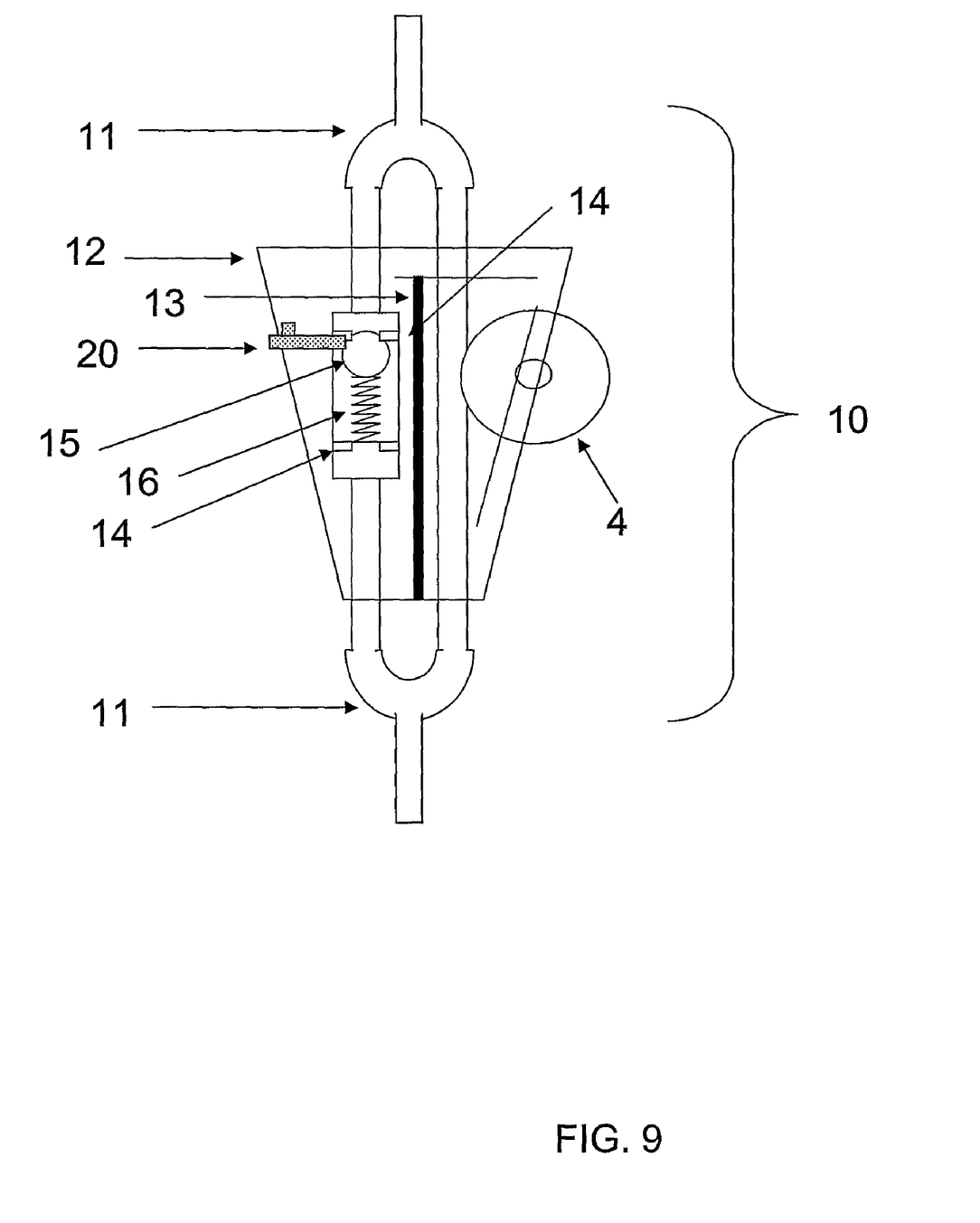
FIG. 9 depicts an exemplary embodiment of a bypass valve with a clip applied to the proximal annular ring.

FIG. 9 demonstrates the IVFBV with a clip 20 applied that distorts the shape of the proximal annular PVC ring.

Figure 10:
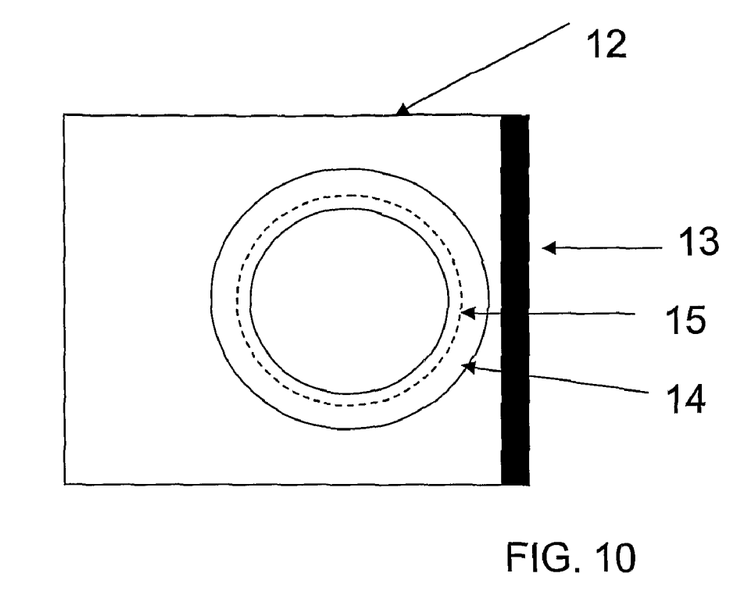
FIG. 10 shows a top view of the proximal annular PVC ring with the ball bearing in place.

FIG. 10 shows a top view of the proximal annular ring, which is in the shape of a doughnut 14 and the ball bearing underneath the ring 15, shown here in a dotted line. The housing 12 contains the septum 13 on the side of the annular ring.

Figure 11:
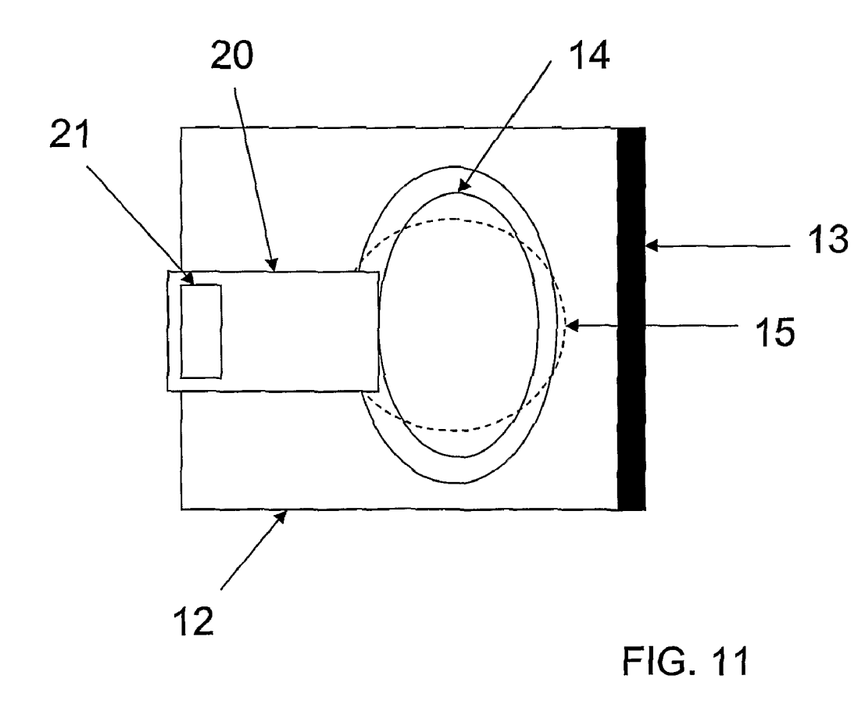
FIG. 11 shows a top view of the proximal annular PVC ring with the ball bearing in place, with the clip distorting the shape of the annular ring.

FIG. 11 shows the annular ring 14 distorted with the clip 20 in place, which allows fluid to enter the valve without pressure applied (either positive or negative). The tab 21 coming off the clip holds the clip in place on the housing 12, and the clip can be removed by detaching the tab from the housing.

I claim:

1. An intravenous fluid administration apparatus comprising:
   a proximal conduit having:
      a spiked first end for attaching to a reservoir of fluid; and
      a second end;
   a distal conduit;
   an intermediate conduit network providing fluid communication from the proximal conduit's second end to the distal conduit and including first and second constituent conduits that provide parallel paths from the proximal conduit to the distal conduit;
   a flow regulator so engaged with the first constituent conduit as to enable control of fluid flow therethrough; and
   a pressure-responsive valve so interposed in the second constituent conduit as to permit flow from the proximal conduit to the distal conduit through the second constituent conduit when a fluid pressure difference across the valve exceeds a threshold and to prevent flow from the proximal conduit to the distal conduit through the second constituent conduit when the fluid pressure difference across the valve does not exceed the threshold.

2. The apparatus of claim 1, wherein the pressure-responsive valve defines an orifice providing fluid communication from the proximal conduit or the second constituent conduit and comprises an occluding element mounted on a biasing element that is biased to hold the occluding element in a position that occludes the orifice.

3. The apparatus of claim 2, wherein the biasing element comprises a spring.

4. The apparatus of claim 3, wherein the occluding element comprises a ball bearing.

5. The apparatus of claim 3, wherein the occluding element comprises a plunger.

6. The apparatus of claim 1, wherein the pressure-responsive valve comprises a duck valve.

7. The apparatus of claim 1, wherein the pressure-responsive valve comprises a one-way flap valve.

8. The apparatus of claim 1, wherein the first and second constituent conduits are contained at least in part in a housing.

9. The apparatus of claim 8, wherein the housing comprises a septum separating the first constituent conduit from the second constituent conduit.

10. The apparatus of claim 1, further comprising an air vent so interposed in the second constituent conduit as to permit air release when fluid flows through the proximal conduit.

11. The apparatus of claim 1, further comprising a bulb pump interposed downstream of the pressure-responsive valve.

12. The apparatus of claim 11, wherein the bulb pump is interposed in the second constituent conduit.

13. The apparatus of claim 11, wherein the bulb pump is interposed in the distal conduit.

14. The apparatus of claim 1, wherein the flow regulator comprises a thumb-wheel regulator.

15. The apparatus of claim 1, wherein the distal conduit defines a sideport.

16. An intravenous fluid administration apparatus comprising:
   a proximal conduit having:
      a spiked first end for attaching to a reservoir of fluid; and
      a second end;
   a distal conduit;
   an intermediate conduit network enclosed at least partly in a housing and providing fluid communication from the proximal conduit's second end to the distal conduit and including first and second constituent conduits that provide parallel paths from the proximal conduit to the distal conduit;
   a thumb-wheel regulator so engaged with the first constituent conduit as to enable control of fluid flow therethrough;
   a pressure-responsive valve:
      so interposed in the second constituent conduit as to:
         permit flow from the proximal conduit to the distal conduit through the second constituent conduit when a fluid pressure difference across the valve exceeds a threshold; and
         prevent flow from the proximal conduit to the distal conduit through the second constituent conduit when the fluid pressure difference across the valve does not exceed the threshold; and
      defining an orifice providing fluid communication from the proximal conduit or the second constituent conduit and comprising a ball bearing mounted on a spring that is biased to hold the ball bearing in a position that occludes the orifice; and
   an air vent interposed in the second constituent conduit distal to the pressure-responsive valve.

17. A method of providing a fluid bolus, comprising:
   placing the apparatus of claim 1 in fluid communication with a vessel in a subject; and
   increasing the fluid pressure difference across the valve to a value exceeding the threshold.

18. The method of claim 17, wherein increasing comprises squeezing a fluid reservoir connected to the proximal conduit.

19. The method of claim 17, wherein increasing comprises creating a negative pressure downstream of the valve.

20. An intravenous fluid administration apparatus comprising:
   a proximal length of tubing having:
      a spiked first end for attaching to a vessel of fluid; and
      a second bifurcating end;
   a first conduit and a second conduit communicating with and extending from respective outlets of the bifurcating end;
   regulator means for controlling a fluid flow rate through the first conduit; and
   valve means for:
      permitting flow through the second conduit from the proximal length of tubing to a distal length of tubing when a fluid pressure difference across the valve means exceeds a threshold; and
      preventing such flow when the fluid pressure difference does not exceed the threshold;
   the distal length of tubing having:
      a rejoining first end in communication with the first conduit and the second conduit; and
      a second end.

* * * * *